United States Patent
Zinn et al.

(10) Patent No.: US 9,746,429 B2
(45) Date of Patent: Aug. 29, 2017

(54) INSPECTION AND REPAIR MODULE

(71) Applicant: SMART APPLICATIONS LIMITED, Wanchai (HK)

(72) Inventors: Michael Trevor Zinn, Pretoria (ZA); Quinton Encombe Woods, Johannesburg (ZA); Petrus Hendrik Buys, Witbank (ZA)

(73) Assignee: SMART APPLICATIONS LIMITED, Wanchai (HK)

( * ) Notice: Subject to any disclaimer, the term of this patent is extended or adjusted under 35 U.S.C. 154(b) by 267 days.

(21) Appl. No.: 14/377,110

(22) PCT Filed: Feb. 28, 2013

(86) PCT No.: PCT/IB2013/051589
§ 371 (c)(1),
(2) Date: Aug. 6, 2014

(87) PCT Pub. No.: WO2013/128396
PCT Pub. Date: Sep. 6, 2013

(65) Prior Publication Data
US 2015/0124237 A1    May 7, 2015

(30) Foreign Application Priority Data
Feb. 28, 2012 (ZA) ................. 2012/01456

(51) Int. Cl.
*G01C 3/08* (2006.01)
*G01N 21/954* (2006.01)
*F23J 99/00* (2006.01)
*G03B 37/00* (2006.01)
(Continued)

(52) U.S. Cl.
CPC ......... *G01N 21/954* (2013.01); *E04G 23/008* (2013.01); *F23J 13/00* (2013.01);
(Continued)

(58) Field of Classification Search
CPC .......... F23J 99/00; F23J 2213/60; F23J 13/00; G01N 21/954; G01N 2201/025; G01N 2201/062; G01N 2201/023; G03B 37/005
(Continued)

(56) References Cited

U.S. PATENT DOCUMENTS 4,855,820 A    8/1989 Barbour
5,362,962 A *  11/1994 Barborak ............... E21B 23/00
                                                       250/234
(Continued)

FOREIGN PATENT DOCUMENTS

DE    212789    8/1984
GB    2293513   3/1996
(Continued)

OTHER PUBLICATIONS

International Search Report from International Application No. PCT/IB2013/051589 mailed Aug. 12, 2013.
(Continued)

*Primary Examiner* — Mark Hellner
(74) *Attorney, Agent, or Firm* — Dorsey & Whitney LLP (57) ABSTRACT

The invention relates to an inspection and repair module for an internal side wall of a vertically erected structure, with the module including a carrier for supporting at least one data recording mechanism and being securable to a hoist, and for an inspection and repair module for an internal wall of a conduit with the module including propulsion means comprising a set of driven tracked wheels controllable by a controller carried by the carrier and configured to provide, within a conduit, longitudinal forward and reverse motion.

26 Claims, 9 Drawing Sheets

(51) Int. Cl.
  *F23J 13/00*   (2006.01)
  *E04G 23/00*   (2006.01)
  *G01C 19/00*   (2013.01)

(52) U.S. Cl.
  CPC ............. *F23J 99/00* (2013.01); *G01C 19/00* (2013.01); *G03B 37/005* (2013.01); *F23J 2213/60* (2013.01); *G01N 2201/023* (2013.01); *G01N 2201/025* (2013.01); *G01N 2201/062* (2013.01)

(58) Field of Classification Search
  USPC ........................................................ 356/4.01
  See application file for complete search history.

(56) References Cited

U.S. PATENT DOCUMENTS

| | | | |
|---|---|---|---|
| 5,663,758 A | 9/1997 | Linville | |
| 6,041,860 A * | 3/2000 | Nazzal | E21B 23/002 166/250.01 |
| 6,249,007 B1 * | 6/2001 | Gooch | G01B 11/026 250/559.29 |
| 2011/0196534 A1 * | 8/2011 | Ekes | F16L 55/48 700/259 |
| 2011/0198075 A1 * | 8/2011 | Okada | G21C 17/017 166/170 |

FOREIGN PATENT DOCUMENTS

| | | |
|---|---|---|
| KR | 1020100002764 A | 1/2010 |
| WO | WO 9944367 | 9/1999 |

OTHER PUBLICATIONS

International Preliminary Report on Patentability from International Application No. PCT/IB2013/051589 mailed May 20, 2014.

* cited by examiner

SECTION A-A

INSPECTION AND REPAIR MODULE

FIELD OF THE INVENTION

This invention relates to an inspection and repair module for industrial applications.

BACKGROUND TO THE INVENTION

Many industrial processes operate at conditions that are harmful to humans. Such processes include infrastructure that require constant monitoring to ensure optimal performance and prevent dangerous conditions from developing.

Such infrastructure includes, for example, smoke stacks, pipes, ducting, shafts, ladles (for molten metal and the like), and raw mineral ore silos.

Apart from the dangerous operating conditions the physical size of the infrastructure also poses challenges to its inspection and repair.

Typically when such infrastructure is inspected a partial or full shutdown of the associated equipment and processes is required. For example, when a power plant smoke stack is conventionally inspected there cannot be any smoke passing through the smoke stack. For its inspection people have to access the inside of the smoke stack to manually inspect the brick work of the smoke stack and detect any problem areas. Any repairs are then done at the same time.

Such an inspection and repair process requires a shutdown of the smoke stack, which puts it out of service for at least one or two days. Even if no problems are found during the inspection which may require repair, the smoke stack is still out of service for a relatively long time.

At a time when energy demand is continuously increasing and the cost of building new plants is extensive and in some instances prohibitive, any unnecessary loss of availability of a smoke stack is a significant problem.

In respect of other industries downtime of processes and equipment due to routine inspection and repair also has a significant impact on the availability of such equipment.

OBJECT OF THE INVENTION

It is an object of the invention to provide an inspection and repair module which at least partly overcomes the abovementioned problem.

SUMMARY OF THE INVENTION

In accordance with this invention there is provided an inspection module for inspecting an internal side wall of a vertically erected structure, the module including a carrier for supporting at least one data recording mechanism and being securable to a hoist.

There is further provided for the module to be securable to the hoist by means of a hook for a cable at an operatively upper end of the module.

There is further provided for the module to include a controller with an associated power source, with the power source preferably carried by the frame, alternatively remotely located from the module and electrically connected to the module, with the controller configured to control the operation of the data recording mechanism.

There is also provided for the data recording mechanism to include at least one recording device comprising a camera, preferably a plurality of cameras, configured to record images, preferably video, of the surroundings of the module, operatively recording images of the internal side wall of a vertically erected structure in which the module is deployed to inspect.

There is further provided for the data recording mechanism to include one or more or a combination of high definition, thermal imaging, infra-red cameras, and multi quantifying cameras, operatively for use in optical surface inspection and making use of defect detection technology associated with the module.

There is further provided for the data recording mechanism to be carried by a collar rotatably secured to the carrier, preferably including at least one light associated with the data recording mechanism, more preferably a high lux light providing light in excess of 1100 lux.

There is still further provided for the data recording mechanism to include one or more of a sonar and ultrasound wall thickness probe, and preferably for the wall thickness probes to also include associated lights.

There is further provided for the module to include communication means comprising at least a data signal transmitter, more preferably a data signal transmitter and receiver, alternatively data input and output ports accessible by means of cables having complimentary plugs, the cable preferably being heat and chemically shielded which is connected to the controller.

There is also provided for the module to include data storage means, carried by the carrier for storage of data recorded by the data recording mechanism.

There is still further provided for the data recording mechanism to include remote distance determination equipment, preferably in the form of a plurality of laser range finders, and further preferably for each of these range finders to be secured proximate a camera alternatively integrated with a camera, and configured to determine, preferably continuously, the distance from the module to an internal side wall of a vertically erected structure in which the module is deployed to inspect, and to relay such distance measurements to the controller.

There is further provided for the module to comprise an elongate body with a circular cylindrical shape having a longitudinal axis extending from its operative top to its operative bottom, and for the module to include at least four range finders, equidistantly spaced around the circumference of the module and directed radially away from its longitudinal axis, and further preferably also a range finder located in the front end of the module aligned with the longitudinal axis and directed to the front end of the module, and which is configured to determine the distance to a base of a vertically erected structure in which the module is deployed for inspection and to relay distance measurements to the controller.

There is further provided for the body to include a cover substantially surrounding the entire carrier, preferably comprised of a set of panels removably securable around the carrier, and further preferably for the cover panels to be sealed over the module.

There is further provided for the module to include a pressurised gas source associated with it, preferably an inert gas, and a pressure sensor connected to the controller to determine the gas pressure within the module and to control the gas source to release gas to maintain a predetermined gas pressure within the module.

There is further provided for the cover to include observation apertures covered with heat and abrasion resistant and heat transfer insulated transparent shields over the data recording mechanism devices and range finders.

The invention further provides for the module to include lighting means for its surroundings, preferably associated with the data recording mechanism devices; and further preferably for a light to be located proximate each camera and directed through the transparent shield proximate each data recording mechanism devices.

According to an alternative feature of the invention the module is provided with a series of equidistantly spaced apart stationary circumferential lights, preferably high lux lights each providing light in excess of 1100 lux, and more preferably for the lights to be arranged in a collar located adjacent to the data recording mechanism, and most preferably for a light collar to be located above and below the data recording mechanism.

The invention further provides for the module to include rotational stabilising means, preferably including a plurality of pivotally adjustable rudders extending from the module, the rudders being equidistantly spaced apart around the circumference of the module, and further preferably for the module to include four rudders.

There is further provided for the rotational stabilising means to include a set of two gyroscopes, a first of which comprises a steering gyroscope and a second of which comprises a sensing gyroscope.

There is further provided for the steering gyroscope to be configured to effect rotation of the module around its longitudinal axis, and for the sensing gyroscope to be configured to measure rotation of the module around its longitudinal axis and relay this measurement to the controller, and for the controller to be configured to control the operation of the steering gyroscope in response to measurements from the sensing gyroscope.

There is further provided for the stabiliser to comprise a magnetic stabiliser.

According to a further feature of the invention there is provided for the power source to comprise a battery, preferably a lithium ion battery pack, carried by the frame.

There is further provided for the module to be provided with a set of rotatable blades secured to a shaft for rotational stability of the module, which preferably extends from the operative top end of the module, and further preferably for the shaft to be connected to a generator, operatively connected to the battery operatively to charge the battery upon rotation of the shaft by the blades as a result gas flow over the blades.

According to a still further feature of the invention there is provided for the module to include attachment means for repair apparatus comprising a turret from which a nozzle rotatably and pivotally extends, the nozzle being in fluid communication with a pressurised supply of fluidic repair material, and further for the repair apparatus operatively to be connectable to the controller for control thereby.

There is further provided for the module to include a closable port configured to receive a feed pipe secured to the supply of fluidic repair material, and for the port to be removably connectable to the nozzle of the repair module, preferably by means of a fluid conduit contained within the module.

There is further provided for the fluidic repair material to comprise one or more of gunite, shotcrete, sprayable concrete, water, blasting grit and compressed air, and still further for the repair apparatus to include a rotatable and pivotable welding torch.

The invention also provides for the cover of the module to be at least partly removable to expose attachment means for the repair apparatus, including a mounting bracket and a fluid conduit connector, and preferably for the repair apparatus to include a cover complementary to the remainder of the cover of the module with the removable portion removed.

According to a yet further feature of the invention there is provided for the module to include propulsion means, including one or more of a hoist control and a set of driven tracked wheels, controllable by the controller and configured to provide propulsion of the module within a structure, and preferably, within a conduit, longitudinal forward and reverse motion by means of traction provided by the tracked wheels, and within a substantially vertical structure up and down hoisting.

There is further provided for each set of tracked wheels to be secured to an extension from the carrier, and for the tracked wheels to be arranged longitudinally in line with the central axis of the module, for a plurality of sets of tracked wheels to be equidistantly spaced around the module, and preferably for the module to include four sets of tracked wheels.

There is further provided for each wheel set to be extendable between retracted and extended positions, and for the extension to be controlled by the controller.

There is further provided for the wheel sets to be provided with pressure and extension sensors, measuring the extent and pressure with which each wheel set is extended towards and against a surface, and for these pressure and extension measurements to be relayed to the controller to control the extent and pressure to which with each wheel set is extended to ensure sufficient traction between the tracked wheels on each wheel set and the surface against which it is extended and to control the alignment of the module within a conduit the module is deployed to inspect, and further preferably for this module to also be configured to receive a repair module as defined above.

In accordance with a further feature of the invention there is provided an inspection and repair system comprising an inspection and repair module as defined above, a remote controller, and a hoist with a cable securable to the cable attachment means of the module.

There is further provided for the system to include a carriage securable to a rim of circular structure to be inspected, for the carriage to include drive means to controllably move the carriage around the rim and a hoist controller to controllably lower and raise the module within the structure.

According to a still further feature of the invention there is provided a method of internally inspecting a side wall of a vertically erected structure comprising securing suspension means on a rim of the structure, suspending an inspection module as defined above from the suspension means, lowering the module into the structure and recording images of the side wall of the structure using a data recording mechanism carried by the module, and directing the module out of the structure.

There is further provided for the method to include receiving at a remote control unit connected to and in communication with the module data feedback from the recording mechanism relating to the structure, and providing directional and rotational stability control instructions to the module, and preferably for the suspension means to comprise a hoist with a hoist control operable by the remote controller.

The invention further provides a method of internally inspecting an internal wall of a conduit comprising directing an inspection module having tracked wheels as defined above into the conduit, and recording images of the wall of the conduit using a data recording mechanism carried by the module, and directing the module out of the structure.

There is further provided for the method to include receiving at a remote control unit connected to and in communication with the module data feedback from the recording mechanism relating to the structure, and providing directional and rotational stability control instructions to the module.

There is still further provided for the method to include directing the tracked-wheel module to a part of the internal wall of a conduit to be repaired, and operating the repair apparatus to repair the designated repair site.

There is further provided for the structure to comprise a smoke stack, cooling tower, chimney, or pipe.

These and other features of the invention are described in more detail below.

BRIEF DESCRIPTION OF THE DRAWINGS

A preferred embodiment of the invention is described by way of example only and with reference to the accompanying drawings in which.

DETAILED DESCRIPTION OF THE INVENTION

Figure 1:
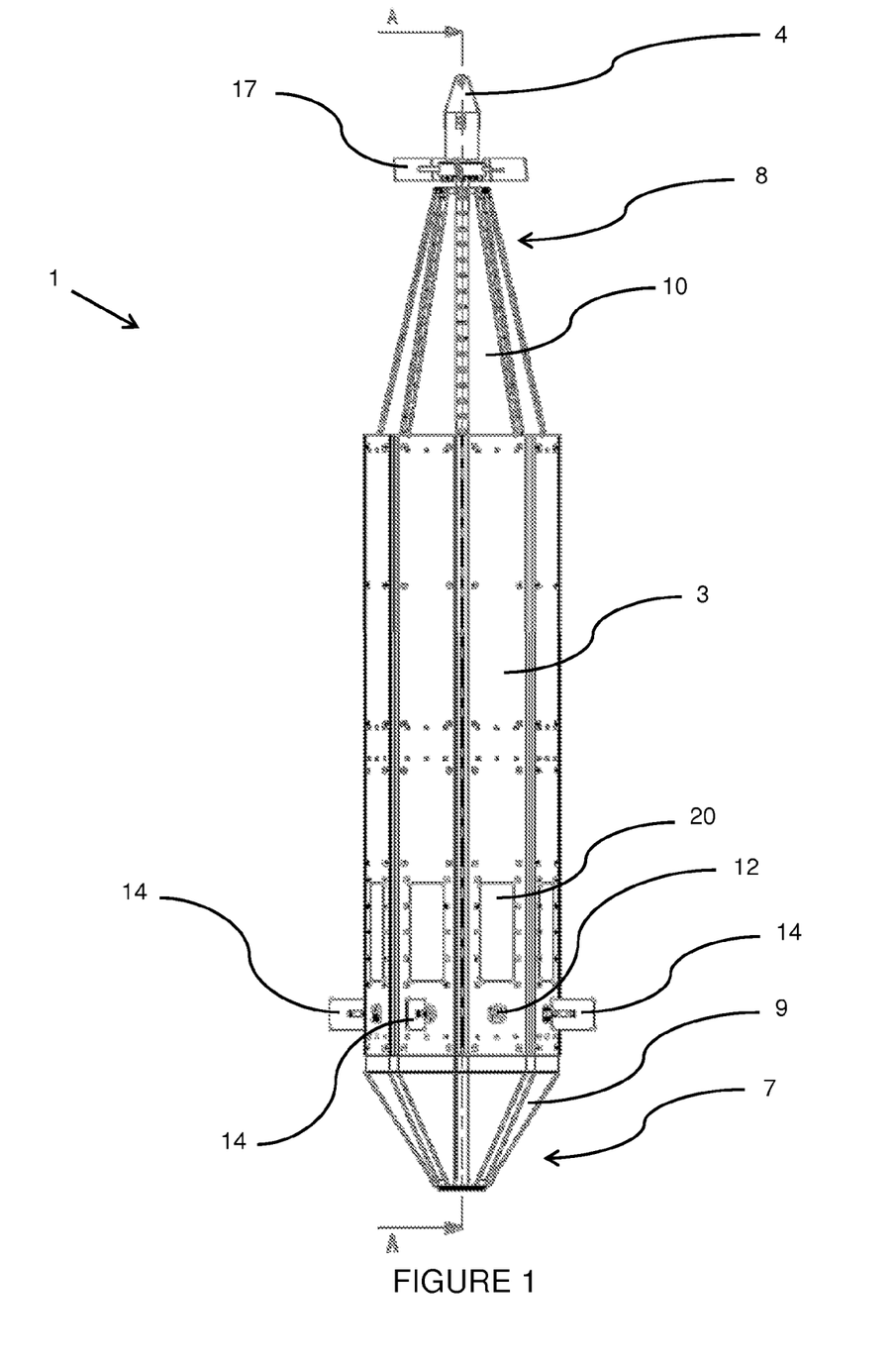
FIG. 1 is a side elevation of a first embodiment of an inspection module according to the invention.
Figure 2:
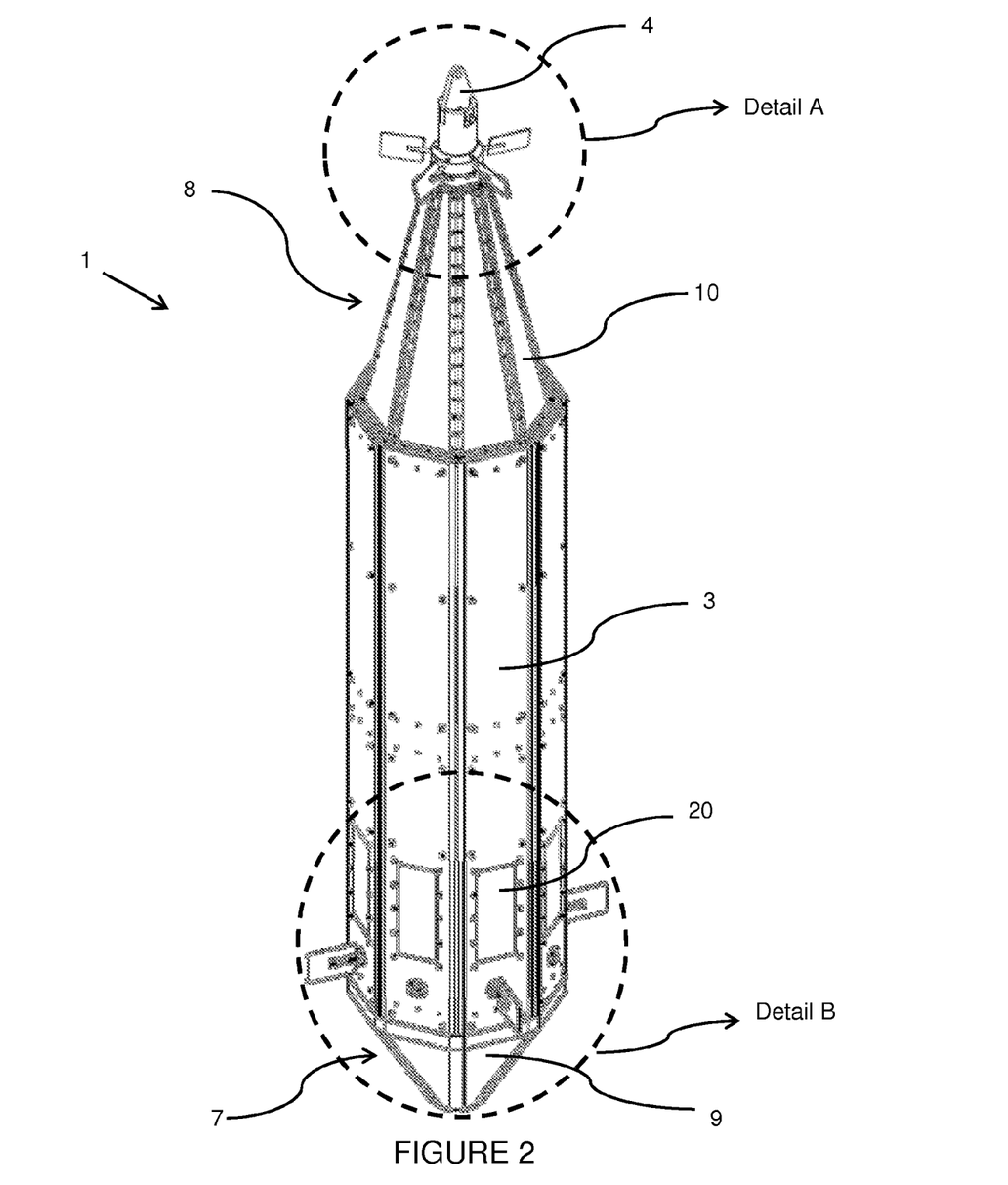
FIG. 2 is rear perspective view of the module of FIG. 1.
Figure 3:
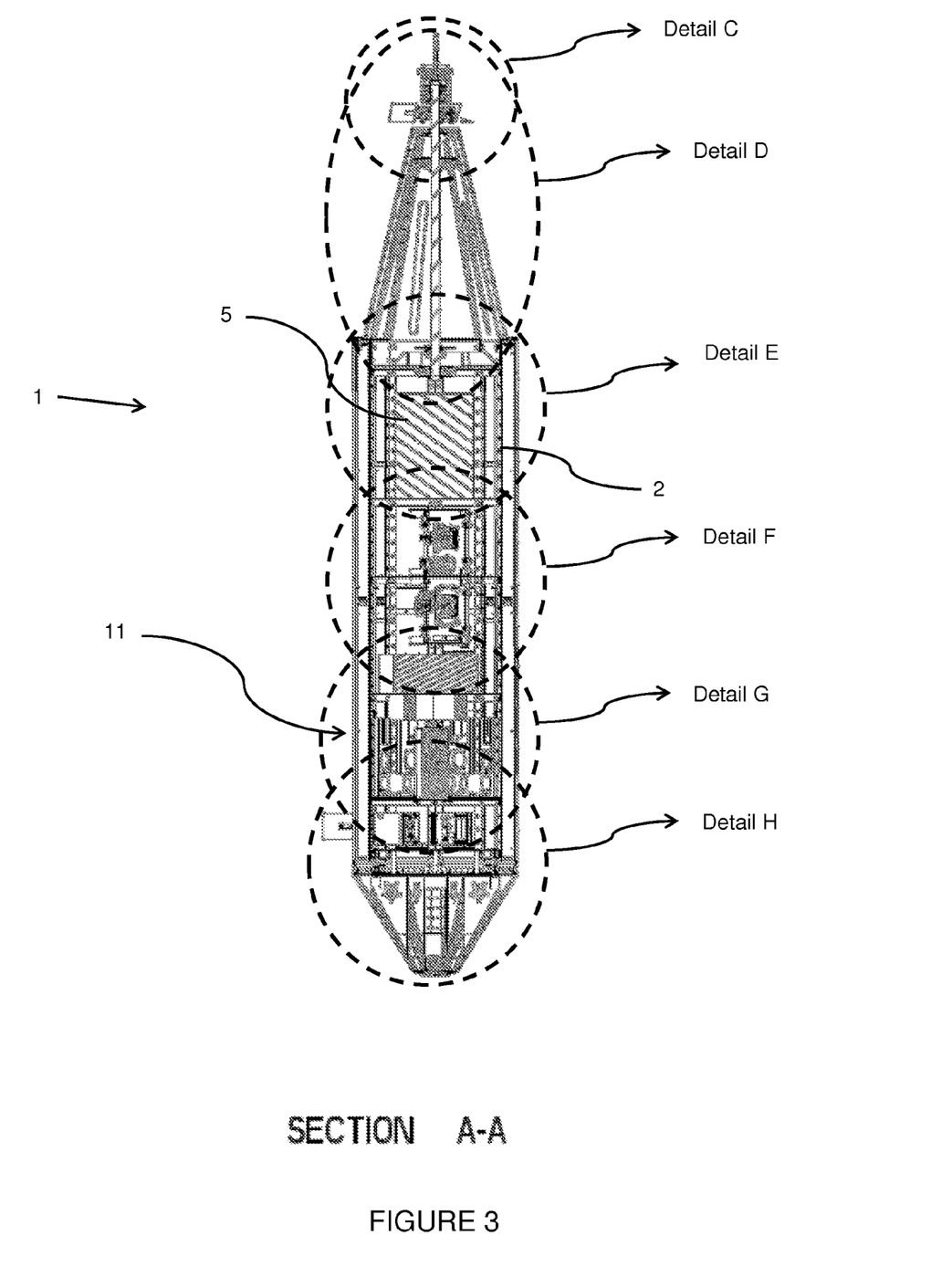
FIG. 3 is a sectional view of the module of FIG. 1.
Figure 4:
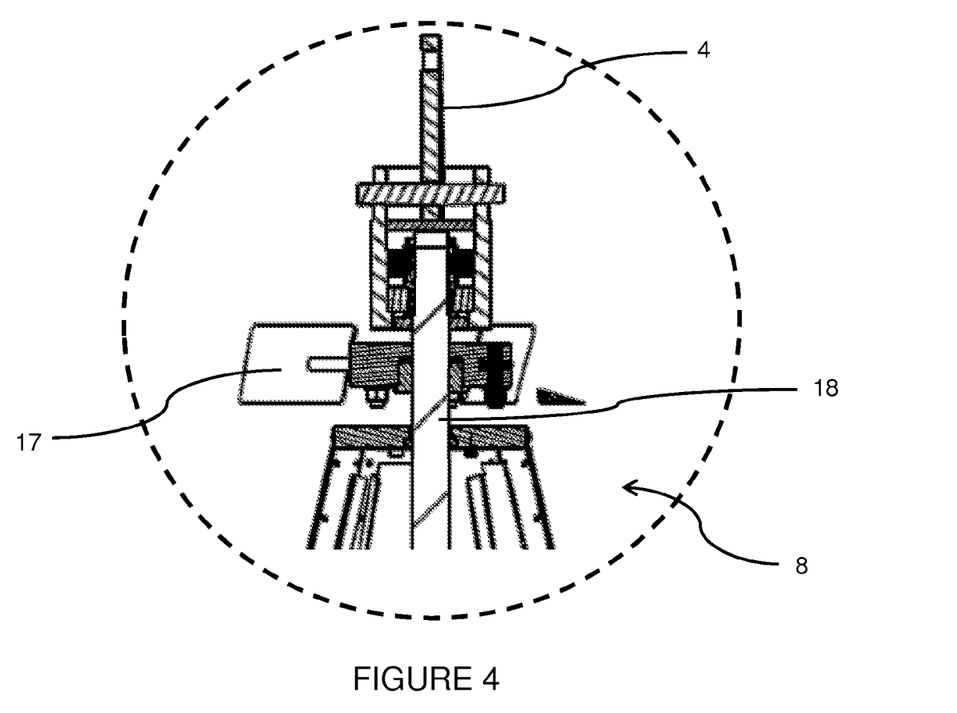
FIG. 4 shows detail C from FIG. 3.
Figure 5:
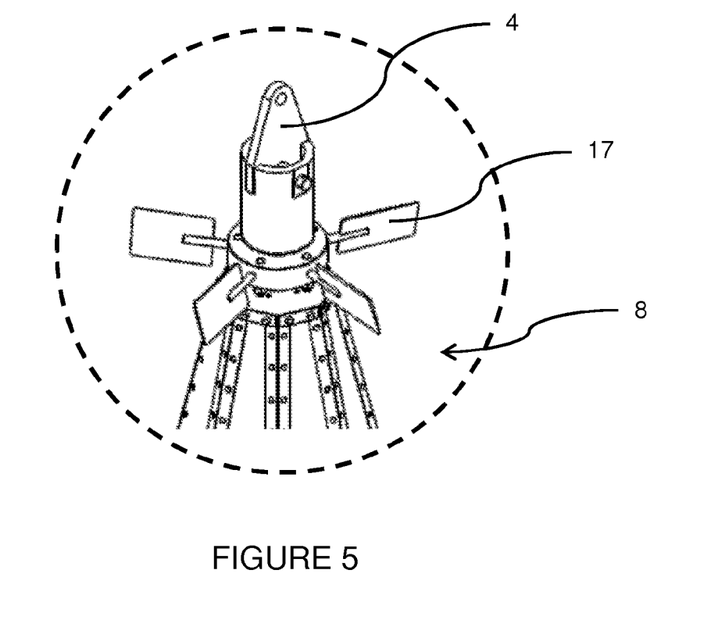
FIG. 5 shows detail A from FIG. 2.
Figure 6:
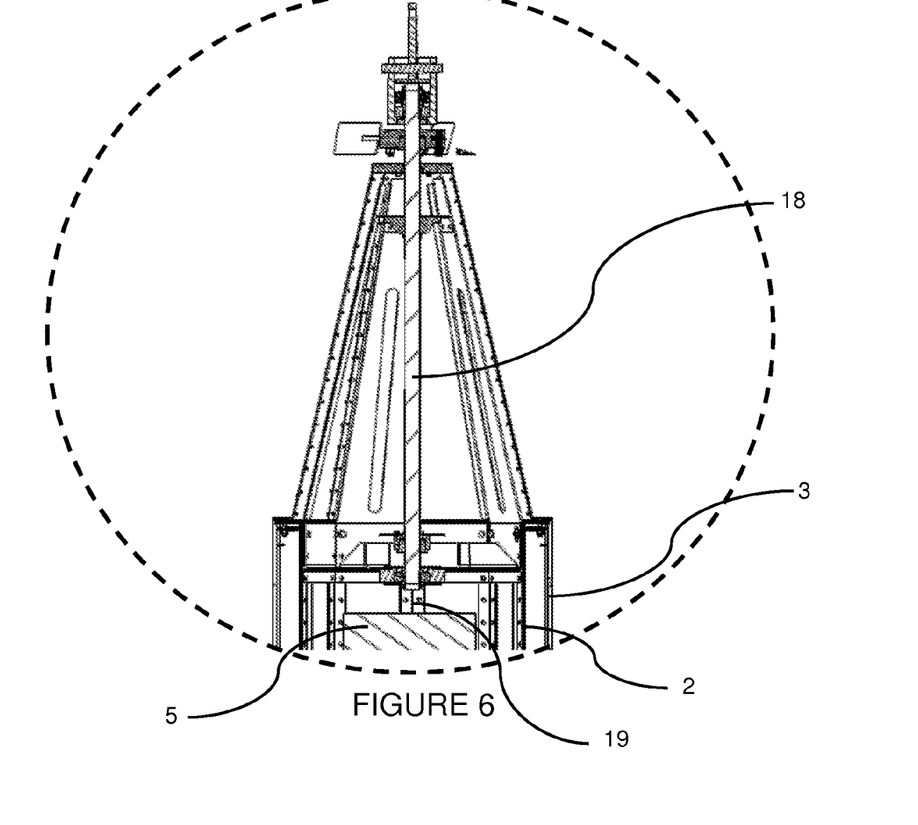
FIG. 6 shows detail D from FIG. 3.
Figure 7:
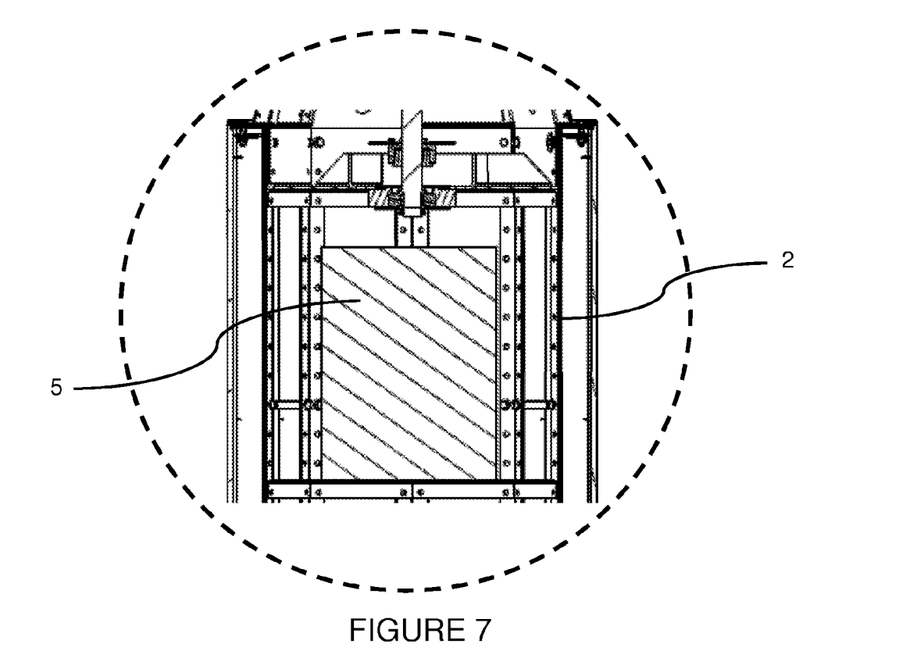
FIG. 7 shows detail E from FIG. 3.
Figure 8:
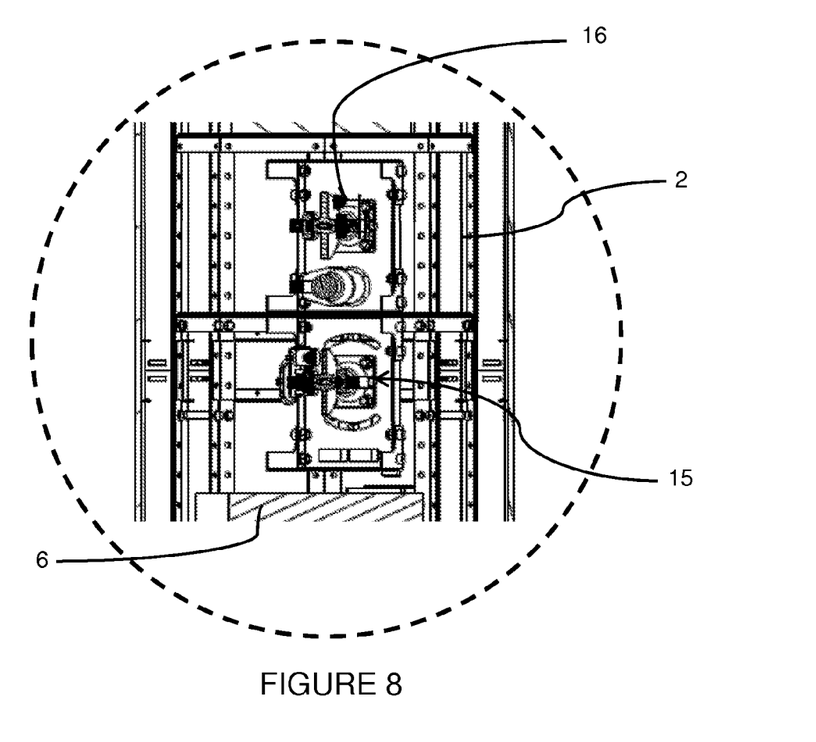
FIG. 8 shows detail F from FIG. 3.
Figure 9:
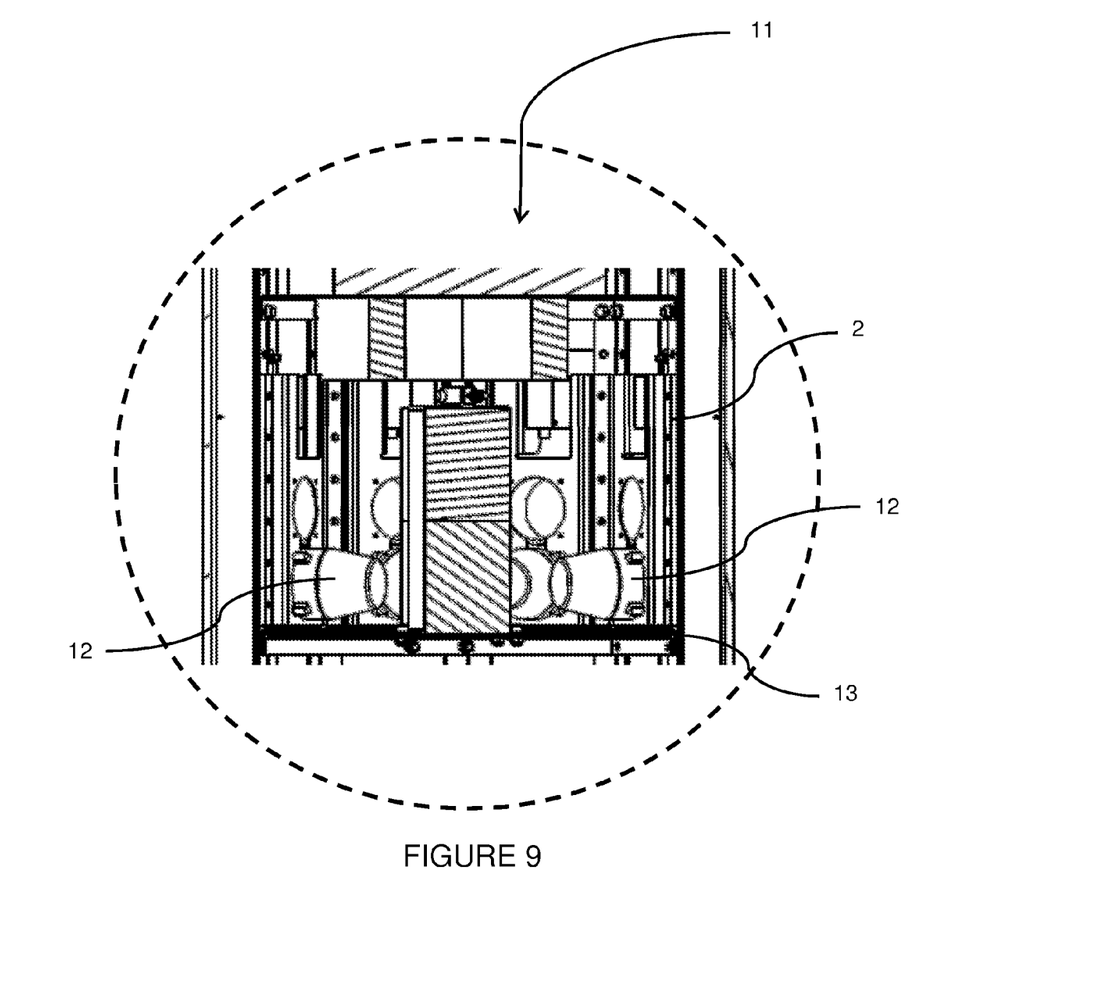
FIG. 9 shows detail G from FIG. 3
Figure 10:
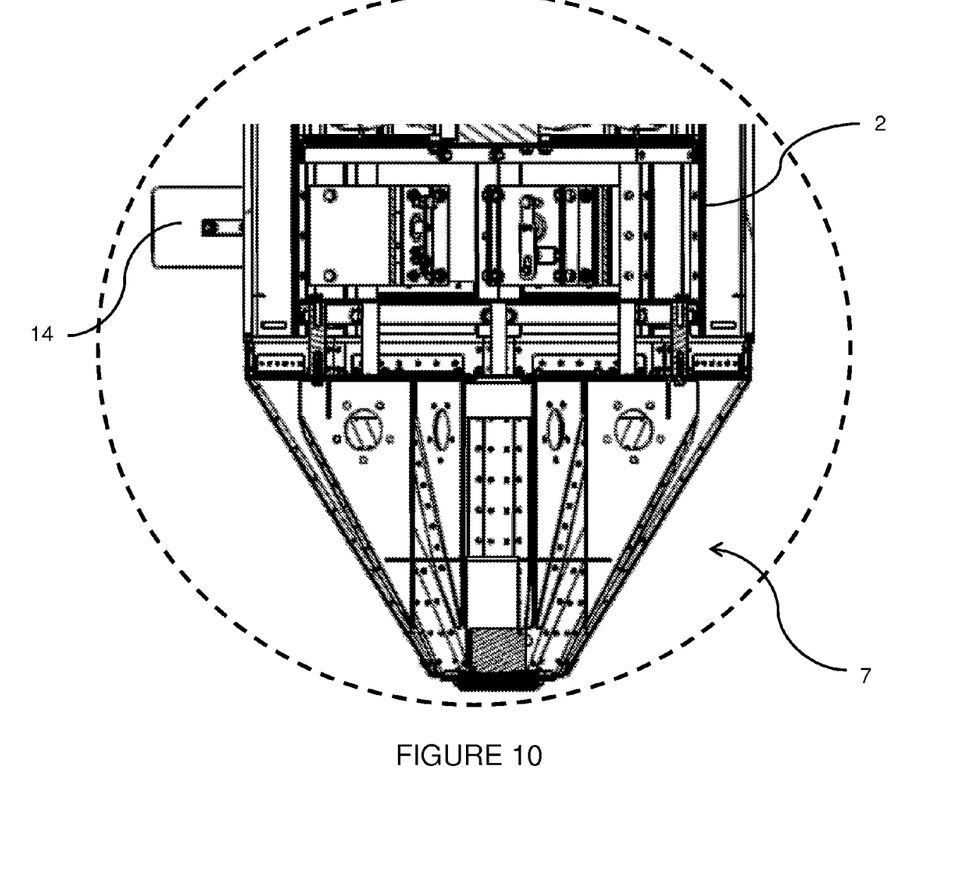
FIG. 10 shows detail H from FIG. 3.
Figure 11:
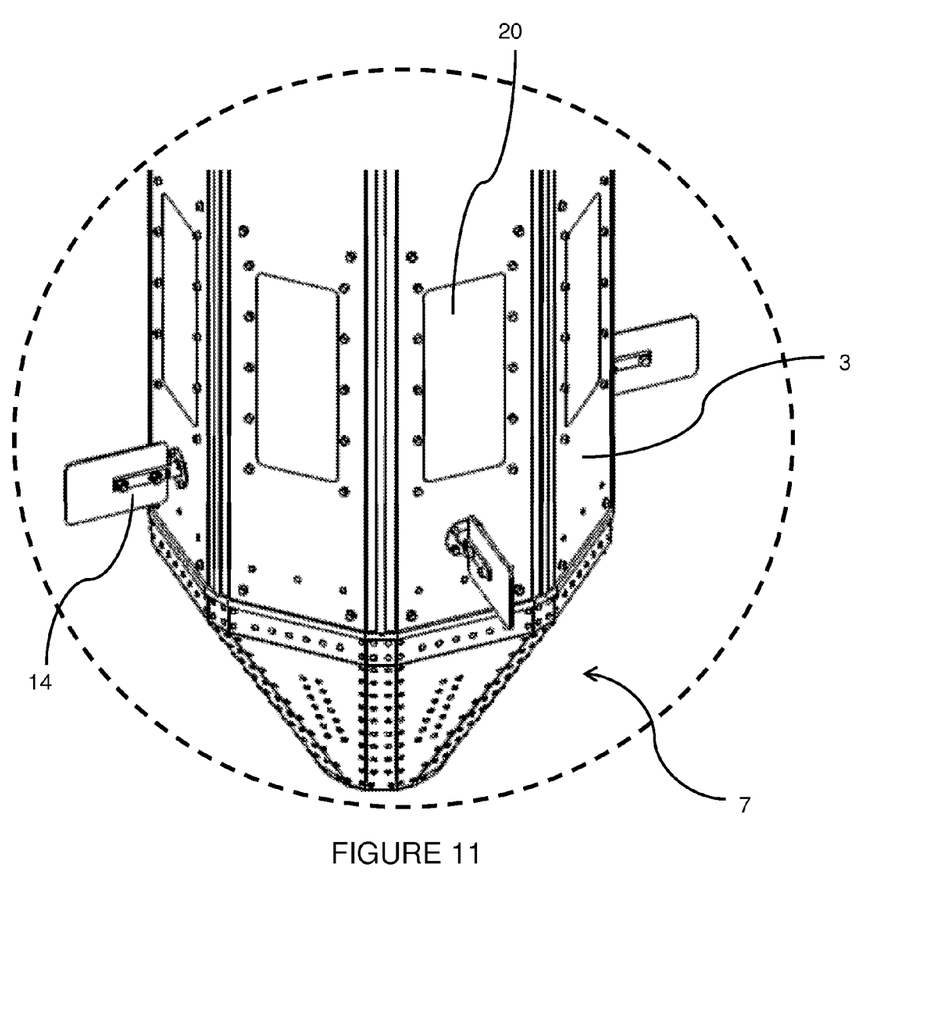
FIG. 11 shows detail B from FIG. 2.

An inspection module (1) according to the invention for use in inspecting a power plant smoke stack is shown in its most basic form in the drawings. The module (1) is designed to be lowered into a smoke stack of a power plant from an overhead hoist. The module (1) may be lowered in close proximity to the side wall of the smoke stack to inspect the inner surface thereof. The hoist (not shown) is secured to a support carriage that is movable around the circumference of the smoke stack rim (not shown), thus allowing the entire smoke stack inner surface to be inspected.

The module (1) comprises a carrier (2) carrying a cover (3) and cable attachment pulley (4), with an internal power supply in the form of a lithium ion battery (5) that is connected to a controller (6) secured to the carrier (2) of the module (1).

The module (1) has a right circular cylindrical shape and has two tapered ends, namely a bottom end (7) and a top end (8). The ends (7, 8) form part of the cover (2) and includes two separate removable covers (9, 10), secured to the carrier (2) of the module (1). The pulley (4) is secured to a cable (not shown) that extends through the top cover (10) from attachment points on the carrier (2).

The shape of the module (1) makes it streamlined, the purpose of which will be discussed further on.

The module (1) also includes communication means in the form of a radio transceiver that is in communication with a radio transceiver (not shown) operated remotely by an operator (not shown), and which forms part of a remote controller (not shown).

The controller (6) is also connected to a data recording mechanism (11) and the communication means. The controller (6) is configured to receive input from data recording mechanism (11) and transmit the input by means of the communication means to the remote transceiver. The controller (6) includes data storage means (not shown) which allows for data received by the data recording mechanism (11) to also be stored on-board the module (1), which is useful as backup in the event that the radio communication is unreliable (which is possible in certain types of structures depending on the materials they are made from).

The data recording mechanism (11) in this basic embodiment it includes a set of cameras (12) and infra-red distance gauges (not shown). The cameras (12) include high definition, thermal imaging cameras, infra-red cameras and multi quantifying cameras. The bottom end (7) of the module is also provided with an infra-red distance gauge (not shown) which determines the distance of the module (1) above the base of a structure that is inspected by it. This allows for accurately controlled lowering of the module (1) within a smoke stack to prevent it from hitting the ground. It also allows for very accurate height determinations to be done of areas within the smoke stack, i.e. on the smoke walls, that are observed to be in need of repair. With known axial orientation and height above the ground, the module can be removed and returned to the exact same spot if required.

The cameras (12) and infra-red distance gauges are mounted on a platform (13) which is secured to the carrier (2). The cameras are also provided with integral LED lights (not shown), and together with the cameras (12), these are equidistantly spaced apart around the module (1). Each high intensity light has an intensity of above 1100 lux.

The cameras (12), infra-red distance gauges and lights are located behind transparent heat resistant shields (20) in the cover (3), which protects them against heat, dust and abrasion and still allows them to capture high definition images and video of the inside of a smoke stack.

The module (1) also includes stabilisers in the form of a set of rudders (14), which is located just behind its front end (7) (which is also the lower end whilst in operation and which faces any gas flow in a smoke stack). Each of the rudders (14) in the set is electrically operable to rotate around a shaft to which it is mounted. These rudders (14) may in use be rotated to a specific orientation with respect to the module (1) to control unwanted rotational movement of the module (1) around its central axis, which may result from gas blowing over the module (1) through a smoke stack. The rudders (14) are used to counter a substantially constant force typically resulting from uneven gas flow in a smoke stack.

The stabilisers further include a set of two gyroscopes (15, 16), a first of which comprises a steering gyroscope (15) and a second of which comprises a sensing gyroscope (16).

The steering gyroscope (15) is configured to effect rotation of the module (1) around its longitudinal axis, and the sensing gyroscope (16) configured to measure rotation of the module around its longitudinal axis and relay this measurement to the controller (6). The controller (6) then uses this data to control the operation of the steering gyroscope (15) to achieve rotational movement of the module (1) around its longitudinal axis or to maintain it in a certain position whilst under force of for example flow of gas over it. The gyroscopes (15, 16) are useful in countering fluctuating forces resulting from sudden changes in gas flow and also for deliberate steering of the module (1).

The module (1) further includes a set of propeller blades (17) at its operative top end (8), which is rotatably secured to a shaft (18) which extends into the module (1). The shaft (18) is connected to a generator (19), which is configured to generate electricity to charge the battery (5). When the module is used in a smoke stack that is still in operation there will be gas flow over it, which will drive the propellers (17) to rotate the shaft (18). This thus generates electricity which is useful to keep the batteries (5) charged, enabling the module (1) to be operated for longer missions.

In use, as discussed above in part already, the module (1) is suspended from a hoist which is secured to a support carriage on the rim of a smoke stack. The module (1) is then lowered into the smoke stack for inspection thereof. The lowering of the module (1) up and down the smoke stack and the movement around its rim are remotely controlled by the operator.

The module controller receives input representing the images captured by the various cameras (12) and distance measurements from the infra-red distance gauges, and transmits this back to the remote controller by means of radio transmission. The radio transmission is received by the remote controller and the images displayed to the operator on a display screen associated with the remote controller. The data stream is processed and analysed and the results presented to the operator. The data relating to the images may also be processed and analysed to provide more information to the operator than what is possible by the visuals alone.

When it becomes necessary for repairs to be performed the module (1) is moved to the top of the stack and swung into an accessible position. The bottom cover (9) is removed and repair apparatus (not shown) is secured to attachment points on the carrier of the module (1). The repair module includes a rotatable and pivotable turret. The turret includes a nozzle that extends from it.

A feed pipe is connected to the module (1) in its top cover (10), into a closable port (not shown). The port (not shown) is connected through the module (1) with the nozzle (not shown). The pipe (not shown) is connected at its other end to a pressurised fluidic repair material supply. This repair material varies depending on the type of repair that is required, and can include any one or more of gunite, shotcrete, sprayable concrete, water, and compressed air.

As mentioned the turret (not shown) is rotatable and pivotable with respect to the central axis of the module (1). The movement of the turret (not shown) is controlled by the stabilisers, which include the gyroscopes (15, 16) and rudders (14) module controller, which in turn is controlled by means of radio frequency by the remote controller. The gyroscopes (15, 16) are also used to counter forces resulting from the operation of the repair apparatus.

This enables the operator to remotely control the nozzle (not shown), allowing him to remotely apply any of the various fluidic repair materials. For example, if an area inside the smoke stack is worn it may be cleaned with water, dried with compressed air, and rebuilt with gunite, shotcrete or sprayable concrete.

When the repair work in one area is done the module (1) may be moved to another area for similar or different repairs.

The above repairs are done when the smoke stack is out of operation.

However, it is possible and desirable to conduct the same whilst the smoke stack is fully operational. This is done by stabilising the module against influence of gas flow through the smoke stack, and insulating and chemically shielding the module and its components against the damaging effects of the gasses, which is done by pressuring the interior of the module with inert gas.

By making use of the module according to the invention it is possible to provide an inspection and repair service of a smoke stack, whilst it is operational. The module is intrinsically safe. It has no flammable liquids or gasses on board and is grounded by means of the supporting cable against static electricity. In addition, the pressurised interior of the module prevents the ingress into the module of gasses that may be present in a structure that is serviced. This protects the module and also isolates the electrical components of the module against such gasses.

It will be appreciated that the embodiments described above are given by way of example only and are not intended to limit the scope of the invention.

The invention claimed is:

1. An inspection module for inspecting an internal side wall of a vertically erected structure, the inspection module comprising:
    a carrier; and
    a controller having an associated power source including a battery, the controller supported by the carrier, the controller configured to control operation of at least one data recording mechanism that includes a plurality of equidistance spaced apart range finders configured to determine a distance from the inspection module to an internal side wall of a generally vertically erected structure in which the inspection module is deployed to inspect and to relay distance measurements to the controller;
    wherein at least one of the plurality of equidistance spaced apart range finders is secured proximate to or integrated with a camera, wherein the at least one of the plurality of equidistance spaced apart range finders substantially continuously relays the distance measurements to the controller;
    wherein the inspection module is securable to a hoist by a hook for a cable at an operatively upper end of the inspection module.

2. The inspection module as claimed in claim 1, further comprising:
    an elongate body having a generally circular cylindrical cross-section and a longitudinal axis extending from an operative top thereof to an operative bottom thereof; and
    a laser range finder located in an operatively bottom end of the inspection module generally aligned with the longitudinal axis and directed away from the operatively bottom end of the inspection module, the laser range finder configured to determine a distance to a base of the generally vertically erected structure in which the inspection module is deployed for inspection and to relay the distance measurements to the controller.

3. The inspection module as claimed in claim 2 wherein the at least one data recording mechanism includes at least one recording device including a camera configured to record images of surroundings of the inspection module, operatively recording images of the internal side wall of the generally vertically erected structure in which the inspection module is deployed to inspect, wherein the camera includes one or more of a high definition, a thermal imaging, infra-red cameras, or multi quantifying cameras, operatively for use in optical surface inspection and making use of defect detection technology associated with the inspection module, and wherein the at least one data recording mechanism includes any one or more of sonar, ultrasound, electromagnetic, or depth detection devices.

4. The inspection module as claimed in claim 3 wherein the at least one data recording mechanism is carried by a collar rotatably secured to the carrier.

5. The inspection module as claimed in claim 4, further comprising at least one light associated with the at least one data recording mechanism.

6. The inspection module as claimed in claim 5, further comprising a plurality of lights arranged in a collar located adjacent to the at least one data recording mechanism, wherein the plurality of lights arranged in the collar are located above and below the at least one data recording mechanism.

7. The inspection module as claimed in claim 1, further comprising:
   communication means including at least a data signal transmitter, wherein the at least a data signal transmitter includes a data signal transmitter and receiver, or data input and output ports accessible by cables having complimentary plugs; and
   a data storage apparatus carried by the carrier for storage of data recorded by the at least one data recording mechanism.

8. The inspection module as claimed in claim 1, further comprising:
   a cover substantially surrounding the entire carrier, the cover including a set of panels removably securable around the carrier or sealed over the inspection module;
   wherein the cover is abrasion resistant and insulated against heat transfer and includes observation apertures covered with transparent shields over the at least one data recording mechanism, the transparent shields being heat resistant;
   a pressurized gas source associated with the inspection module; and
   a pressure sensor connected to the controller to determine gas pressure within the inspection module and to control the pressurized gas source to release gas to maintain a predetermined gas pressure within the inspection module.

9. The inspection module as claimed in claim 1, further comprising rotational stabilizing means.

10. The inspection module as claimed in claim 9 wherein the rotational stabilizing means includes:
    a plurality of pivotally adjustable rudders extending from the inspection module and equidistantly spaced apart around a circumference of the inspection module;
    a steering gyroscope configured to effect rotation of the inspection module around a longitudinal axis thereof and is connected to the controller for control thereof;
    a sensing gyroscope configured to measure rotation of the inspection module around the longitudinal axis and connected to the controller to relay rotational movement measurements to the controller which is configured to control the steering gyroscope in response to measurements from the sensing gyroscope;
    a magnetic stabilizer; and
    a set of rotatable blades secured to a shaft that extend from an operative top end of the inspection module, wherein the shaft is connect to a generator connected to a battery of the power source operatively to charge the battery upon rotation of the shaft by the set of rotatable blades as a result gas flow over the set of rotatable blades.

11. The inspection module as claimed in claim 1, further comprising attachment means for a repair apparatus including a turret from which a nozzle rotatably and pivotally extends, the nozzle being in fluid communication with a pressurized supply of fluidic repair material, and the repair apparatus is operatively connected to the controller for control thereby.

12. The inspection module as claimed in claim 11, further comprising:
    a closable port configured to receive a feed pipe secured to the supply of fluidic repair material;
    wherein the closable port is removably connectable to the nozzle by a fluid conduit contained within the inspection module, wherein the fluidic repair material includes one or more of gunite, shotcrete, sprayable concrete, water, blasting grit, or compressed air;
    wherein at least part of the cover is removable to expose the attachment means for the repair apparatus that includes a mounting bracket, a fluid conduit connector, and a rotatable and pivotable welding torch, wherein at least part of the cover is removable to expose the mounting bracket and is complimentary to a remainder of the cover with the removable portion removed.

13. The inspection module as claimed in claim 1 wherein the generally vertically erected structure includes a smoke stack, a cooling tower, or a chimney.

14. An inspection system for inspecting the internal side wall of the generally vertically erected structure, the inspection system comprising:
    an inspection module as claimed in claim 1;
    a remote controller with an associated power source remotely located from the inspection module, the remote controller configured to communicate through the communication means with the controller of the inspection module to control the operation of the at least one data recording mechanism;
    a hoist with a cable secured to the hook of the inspection module;
    a hoist controller configured to controllably lower and raise the inspection module within the generally vertically erected structure, for inspection thereof through operation of the at least one data recording mechanism; and
    a movable support securable over a rim of a side wall of the generally vertically erected structure in which the inspection module is deployed for inspecting, the movable support including drive means to controllably move the support around the rim.

15. An inspection module for inspecting an internal wall of a conduit, the inspection module comprising:
    a carrier for supporting at least one data recording mechanism that includes a plurality of equidistantly spaced apart range finders each of which is secured proximate to or integrated with a camera, wherein the plurality of equidistantly spaced apart range finders substantially continuously relay the distance measurements to the controller;
    an associated power source; and
    a plurality of sets of driven tracked wheels secured to an extension from the carrier and equidistantly spaced around the inspection module, each of the plurality of sets of driven tracked wheels arranged longitudinally in line with a longitudinal axis of the inspection module and being controllable by a controller carried by the carrier and configured to provide, within the conduit, longitudinal forward and reverse motion;
    wherein the at least one data recording mechanism includes at least one laser range finder configured to determine a distance from the inspection module to the internal side wall of the internal side wall of the conduit in which the inspection module is deployed to inspect and to relay distance measurements to the controller.

16. The inspection module as claimed in claim 15 wherein each of the plurality of sets of tracked wheels is provided with pressure and extension sensors, configured to measure an extent and a pressure with which each of the plurality of sets of tracked wheels is extended towards and against a surface within the conduit that the inspection module is deployed to inspect, and wherein the pressure and extension measurements are relayed to the controller to control the extent and pressure to which each of the plurality of sets of tracked wheels is extended from the carrier to ensure sufficient traction between tracked wheels on each of the plurality of sets of tracked wheels and the surface against which it is extended for controlled forward and backwards motion and to control the alignment of the inspection module within the conduit.

17. The inspection module as claimed in claim 15:
wherein the at least one data recording mechanism includes at least one recording device including one or more cameras configured to record images of the surroundings of the inspection module, operatively recording images of an internal side wall of the conduit in which the inspection module is deployed to inspect;
wherein the one or more cameras include one or more of a high definition, a thermal imaging, an infra-red camera, or multi quantifying cameras, operatively for use in optical surface inspection and making use of defect detection technology; and
wherein the at least one data recording mechanism includes any one or more of sonar, ultrasound, electromagnetic, or depth detection devices, associated with the inspection module.

18. The inspection module as claimed in claim 17 wherein the at least one data recording mechanism is carried by a collar rotatably secured to the carrier.

19. The inspection module as claimed in claim 18, further comprising at least one light associated with the at least one data recording mechanism.

20. The inspection module as claimed in claim 19, further comprising a plurality of lights arranged in a collar located adjacent to the at least one data recording mechanism, wherein the plurality of lights are located above and below the at least one data recording system.

21. The inspection module as claimed in claim 15, further comprising:
communication means including at least a data signal transmitter, wherein the at least a data signal transmitter includes a data signal transmitter and receiver, or data input and output ports accessible by means of cables having complimentary plugs; and
a data storage apparatus carried by the carrier for storage of data recorded by the at least one data recording mechanism.

22. The inspection module as claimed in claim 15, further comprising:
an elongate body having a circular cylindrical cross-section and a longitudinal axis extending from an operative front thereof to an operative rear thereof;
a cover surrounding the entire carrier, wherein the cover includes of a set of panels removably securable around the carrier or sealed over the inspection module, wherein the cover is insulated against heat transfer and includes observation apertures covered with transparent shields over the data recording mechanism devices, wherein the transparent shields are heat resistant;
a pressurized gas source associated with the inspection module; and
a pressure sensor connected to the controller to determine gas pressure within the inspection module and to control the gas source to release gas to maintain a predetermined gas pressure within the inspection module.

23. The inspection module as claimed in claim 15, further comprising attachment means for a repair apparatus including a turret from which a nozzle rotatably and pivotally extends, the nozzle being in fluid communication with a pressurized supply of fluidic repair material, and the repair module is connectable to the controller for control thereby.

24. The inspection module as claimed in claim 23, further comprising:
a closable port configured to receive a feed pipe secured to the supply of fluidic repair material, wherein a port is removably connectable to the nozzle by means of a fluid conduit contained within the inspection module;
wherein the fluidic repair material includes one or more of gunite, shotcrete, sprayable concrete, water, blasting grit, or compressed air; and
wherein at least part of the cover is removable to expose the attachment means for the repair apparatus which includes a mounting bracket, a fluid conduit connector, and a rotatable and pivotable welding torch, wherein at least part of the cover is removable to expose the mounting bracket and is complimentary to a remainder of the cover with the removable portion removed.

25. An inspection system for inspecting the internal wall of the conduit, the inspection system comprising:
an inspection module as claimed in claim 15; and
a remote controller with an associated power source remotely located from the inspection module and configured to communicate with the controller of the inspection module to control operation of the at least one data recording mechanism and motion of the inspection module within the conduit.

26. A method of internally inspecting a side wall of the generally vertically erected structure, the method comprising:
securing suspension means on a rim of the generally vertically erected structure;
suspending an inspection module as claimed in claim 1 from the suspension means;
lowering the inspection module into the generally vertically erected structure;
recording images of the side wall of the generally vertically erected structure using the at least one data recording mechanism carried by the inspection module; and
directing the inspection module out of the generally vertically erected structure.

* * * * *